United States Patent [19]

Downing et al.

[11] Patent Number: 5,124,662
[45] Date of Patent: Jun. 23, 1992

[54] PARTICLE CLASSIFICATION EMPLOYING PLANE POLARIZED RADIATION APPLIED IN THREE ORTHOGONAL DIRECTIONS

[76] Inventors: Barry J. Downing, 20 Berg Road, Fish Hoek, Cape Province; John D. Salter, A007 Downsview, Linden Road, Sandown, Sandton, Transvaal, both of South Africa

[21] Appl. No.: 600,325

[22] Filed: Oct. 19, 1990

[30] Foreign Application Priority Data

Oct. 19, 1989 [ZA]  South Africa ............... 89/7921

[51] Int. Cl.$^5$ .................. G01N 22/00; B07C 5/00
[52] U.S. Cl. .................... 324/636; 324/631; 209/576
[58] Field of Search ............... 324/629, 631, 633, 636, 324/71.4; 377/11, 12; 209/576, 577

[56] References Cited

U.S. PATENT DOCUMENTS

| | | | |
|---|---|---|---|
| 3,458,808 | 7/1969 | Agdur | 324/633 |
| 4,885,527 | 12/1989 | Lacombe et al. | 324/636 |
| 4,899,100 | 2/1990 | Talanker et al. | 324/636 |

*Primary Examiner*—Jack B. Harvey
*Attorney, Agent, or Firm*—Scully, Scott, Murphy & Presser

[57] ABSTRACT

In the method, particles (16) are classified by locating them in a resonance cavity (10) and applying a swept range of microwave radiation to the cavity. The transmitted signals are detected and analyzed. The particle is then assigned to a classification in accordance with changes in the dielectric characteristics of the cavity as a result of the presence of the particle. The radiation is polarized and is applied in at least two mutually orthogonal directions. With the particle located at the center of the cavity, where the E-field is a maximum, and with signals propagating in at least two mutually orthogonal direction, account is taken of dimensional and orientational inaccuracies from particle to particle.

12 Claims, 2 Drawing Sheets

PARTICLE CLASSIFICATION EMPLOYING PLANE POLARIZED RADIATION APPLIED IN THREE ORTHOGONAL DIRECTIONS

BACKGROUND TO THE INVENTION

This invention relates to a method and apparatus for classifying particles.

It has already been proposed in UK patent applications 2211299A and 2230099A to classify particulate material by using, as a classification criterion, the change in dielectric constant of a cavity due to the presence therein of a particle which is to be classified. In each case, the cavity is subjected to a swept frequency range of electromagnetic radiation while the particle is located therein and the signals transmitted by the cavity are detected and analysed. The particles are then classified, and possibly subsequently sorted into fractions, in accordance with the change in dielectric constant of the cavity attributable to the presence of the particle. The change in dielectric constant manifests itself as a change in the resonant frequency of the cavity, as a change in the amplitude of the transmitted signal at resonance.

The electromagnetic radiation is plane polarised and applied to the cavity in a manner giving rise to a specific electric field in the cavity. The electric field exists in a specific distribution and the effect on the dielectric characteristics of the cavity will depend on the shape and orientation of the particle and its relationship to the particular electric field distribution. Thus different particle shapes and/or orientations may give rise to inaccuracies in the classification because of the different relationships with the specific electric field which exists in the cavity.

SUMMARY OF THE INVENTION

A first aspect of the invention provides a method of classifying a particle comprising the steps of applying a swept frequency range of electromagnetic radiation to a cavity while the particle is in the cavity, detecting and analysing the signals transmitted by the cavity and assigning a classification to the particle in accordance with changes in the dielectric characteristics of the cavity caused by the presence of the particle, characterised in that the electromagnetic radiation is applied to the cavity in at least two mutually orthogonal directions.

In the preferred version of the invention, the cavity is cube-shaped and the particle is located at least temporarily at the centre of the cavity.

In a sorting application, a stream of particles may be passed one by one through the centre of the cavity in a direction extending from one corner of the cube-shape to the diagonally opposite corner thereof. Alternatively, the particles of the stream may be passed through the cavity in a direction extending from the centre of one face of the cube-shape to the centre of the opposite face thereof. In a single particle classification system, a single particle only may be located on a support at the centre of the cavity for testing.

With the cube-shaped cavity, plane polarised radiation can be applied to the cavity in three mutually orthogonal directions.

As a less preferred alternative to the cube-shaped cavity, the cavity can be round cylindrical in shape, the particle being located at least temporarily at the centre of the round cylindrical shape. In the case of the round cylindrical cavity, a stream of particles can be passed one by one through the cavity in a direction transverse to the axis, and circularly polarised radiation is applied axially to the cavity. In all cases, it is preferred that the radiation is in the microwave part of the electromagnetic spectrum. The particle may be classified in accordance with detected changes in the resonant frequency of the cavity, in signal amplitude at resonance or in Q-factor.

A second aspect of the invention provides apparatus for classifying particles, the apparatus comprising a resonant cavity, means for applying a swept range of electromagnetic radiation to the cavity while each particle is in the cavity, means for detecting and analysing the signals transmitted by the cavity and means for assigning a classification to the particle in accordance with changes in dielectric characteristics of the cavity caused by the presence of the particle, characterised by means for applying the radiation to the cavity in at least two mutually orthogonal directions.

One form of cube-shaped cavity has an entry opening at one corner of the cavity and an exit opening at the diagonally opposite corner, the apparatus including means for passing a stream of particles one by one through the centre of the cavity in a direction from the entry opening to the exit opening. In another form of cube-shaped cavity, the cavity has entry and exit openings located centrally in opposite faces of the cube-shape. Yet another form of cube-shaped cavity has an access opening in one face of the cube shape through which individual particles can be introduced into the cavity, the cavity including a support at the centre thereof to support the particle for testing.

In the case of a round cylindrical cavity, the cavity may have entry and exit openings through which particles can pass in a direction transverse to the axis of the cavity, the apparatus including means for passing a stream of particles one by one through the cavity via the entry and exit openings.

BRIEF DESCRIPTION OF THE DRAWINGS

The invention will now be described in more detail, by way of example only, with reference to the accompanying drawings in which.

DESCRIPTION OF EMBODIMENTS

Figure 1:
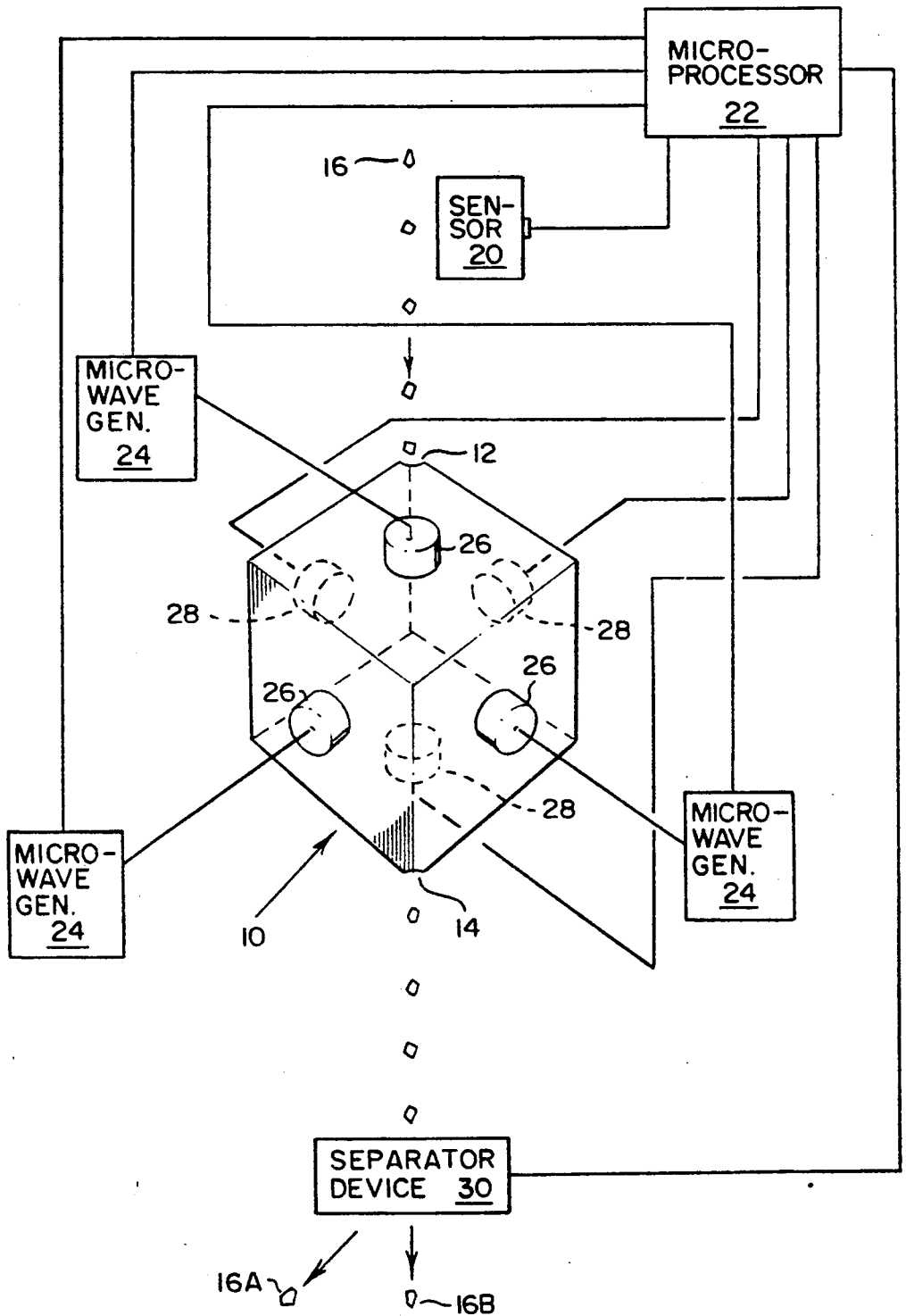
FIG. 1 shows a schematic diagram illustrating a first embodiment of the invention.

FIG. 1 shows a cube-shaped cavity 10 having a non-radiating entry opening 12 at one corner and a non-radiating exit opening 14 at the diagonally opposite corner. Particles 16 of a particulate mass which is to be classified are passed through the centre of the cavity 10 in a direction extending diagonally from the entry opening 12 to the exit opening 14. This may be achieved in any convenient manner, for instance by causing the particles to fall one by one under gravity along the required path. The particles may be organised into a stream, in which the particles are spaced apart in the direction of the stream, on a conveyor belt and then be projected in free flight from the conveyor belt so as to fall through the cavity 10 one after the other. A sensor 20 is provided to detect when a particle 16 is about to enter the cavity and to send a signal indicative of this fact to a central processor 22. In response to the signal from the sensor 20, the microprocessor 22 simultaneously energises three microwave generators 24 which each apply a pulse or continuous wave of plane polarised microwave radiation to the cavity in three mutually orthogonal directions via three appropriate transmission line structures 26 located at different faces of the cubic cavity 10. On opposite faces of the cubic cavity 10 are located microwave detectors 28 which detect the radiation transmitted by the cavity and which feed signals indicative of the detected radiation to the processor 22.

The transmission line structures 26, the detectors 28, the non-radiating openings 12 and 14 and the side dimension of the cubic cavity 10 are all selected in accordance with the particular frequency range under consideration and in accordance with known theoretical principles. In a typical test apparatus, the cube-shape had a side length of 300 mm and the openings 12 and 14 a side length of about 70 mm. Of course, the latter dimensions will depend in each practical case on the size of the particles which are to be classified by the apparatus.

The central processor 22 analyses the signals from the detectors 28 and classifies the particle. In a particle sorting apparatus, the processor 22 may be arranged to operate a separation device 30 at a downstream location to separate particles into fractions in accordance with the classifications assigned to them. In one example, the downstream separation device may comprise a fluid blast ejection system which issues a short duration blast of fluid, typically air, at the appropriate instant to separate certain particles 16A from the remaining particles 16B by deflecting those particles out of the falling stream of particles.

In the case of each pulse or continuous wave of microwave radiation, the electric field will be at right angles to the direction of propagation of the radiation through the cavity. Normally, the three electric fields which are created by the three distinct pulses or waves will overlap and interfere with one another, the maximum field being at the centre of the cavity. Thus the particles, which move through the centre of the cavity, will be subjected to all three fields at the centre. Accordingly, the exact shape or orientation of the particle, which could have a marked effect on a single field because of the distribution thereof, will have little effect on the combined responses of the three detectors 28. In other words, by causing the particle to move through three mutually orthogonal fields, the shape and orientation of the particle will in effect be averaged out in the combination of signals sent to the processor 22.

The microprocessor performs a classification exercise based upon any one or more of a variety of different criteria related to the change in the dielectric characteristics of the cavity due to the presence of the particle therein. The basis may, for instance, be a change in the resonant frequency of the cavity, a change in the transmitted signal amplitude at resonance, or a change in the Q-factor at resonance. Of course, with the present apparatus, the processor 22 will perform the classification exercise using a combination of the signals received from the three detectors 28.

The cavity 10 may possibly be of split construction as described in UK patent application 2230099A, the contents of which are incorporated herein by reference. The split in this case will be in a plane dividing the cavity diagonally.

Figure 2:
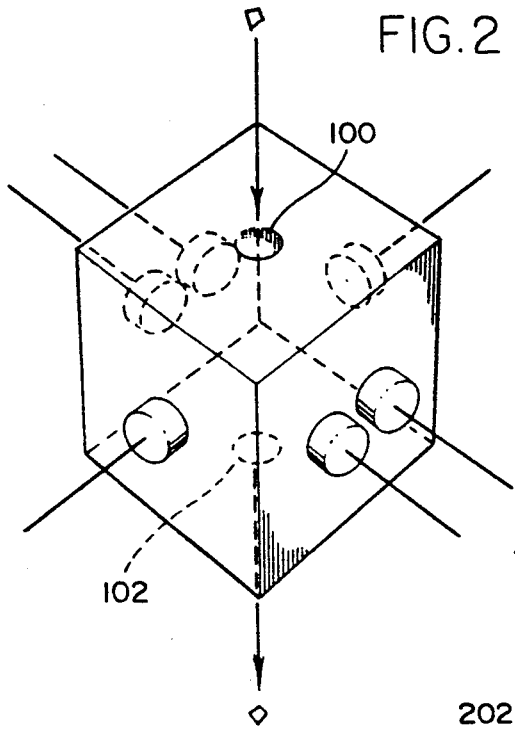
FIG. 2 shows a view of the resonant cavity of a second embodiment of the invention.

FIG. 2 shows the resonant cavity of a second embodiment. In this case, the cavity is again cube-shaped. However, the particles are passed through the cavity via entry and exit openings 100 and 102 located centrally in opposite faces of the cube-shape. Transmission line structures are provided to apply plane polarised microwave radiation in three mutually orthogonal directions, but in this case, two of the transmission line structures are provided at one face of the cube-shape with appropriate detectors on the opposite face. A third transmission line structure and detector are provided in the remaining faces of the cube shape.

Figure 3:
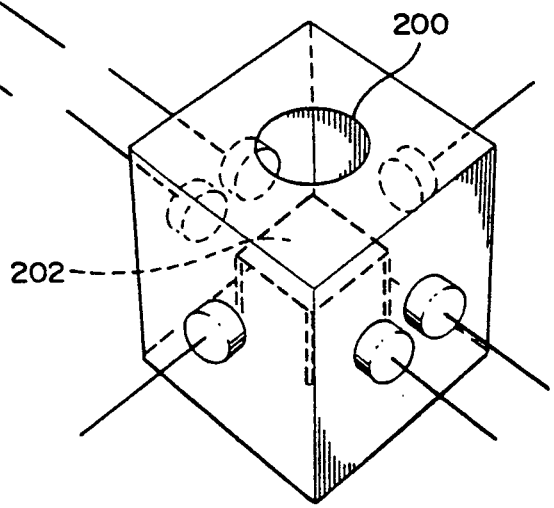
FIG. 3 shows a view of the resonant cavity of a third embodiment of the invention.

FIG. 3 shows a third embodiment which has many similarities to the second embodiment. This embodiment is intended for testing of individual particles rather than a stream of particles in a sorting apparatus. In this case, there is a large access opening 200 in one face of the cavity through which a single particle can be introduced into the cavity. A central support 202 is provided for supporting the particle at the centre of the cavity for testing purposes. The material of the support 202 is chosen to produce a known change in the relevant dielectric characteristic of the cavity so that account can be taken of the dielectric variations attributable to the presence in the cavity of the support. A suitable material for the support is TEFLON. After the test is completed and a classification has been assigned to the particle, it is removed through the access opening 200.

Figure 4:
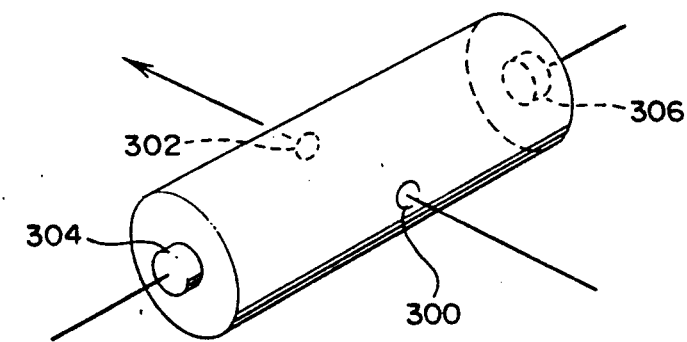
FIG. 4 shows a view of the resonant cavity of a fourth embodiment of the invention.

FIG. 4 shows a fourth embodiment in which the cavity is round cylindrical in shape. A stream of particles is caused to move transversely through the cavity via an entry opening 300 and an exit opening 302. Circularly polarised microwave radiation is applied axially to the cavity using a transmission line structure 304. The transmitted radiation is detected by a detector structure 306. The radiation propagates through the cavity in a corkscrew manner. With the circularly polarised radiation, the propagation of the radiation is effectively in two directins that are mutually orthogonal to one another i.e. axially and in a circle. Although this system is still preferred to a system in which radiation is propagated in one direction only, it will be appreciated that inaccuracies could still arise because of dimensional and orientational variances in the third dimension of the particle.

The apparatuses of FIGS. 1, 2 and 4 are suitable for sorting particulate ore material into fractions. In one specific example, diamond or diamond bearing particles can be sorted quickly and efficiently from non-diamond particles. The apparatus of FIG. 3 is suitable for testing individual particles, for example, mineral samples recovered during geological exploration. In such applications, the access opening 200 could have a diameter of about 15 mm to enable a person's hand to be inserted to place the sample in, and recover it from, the cavity. In practice, the access opening 200 will be closed off with a suitable closure during actual testing of a particle.

We claim:

1. A method of classifying a particle comprising the steps of locating the particle at least temporarily at a center of a cavity, applying a swept frequency range of plane polarized electromagnetic radiation to the cavity in three mutually orthogonal directions while the particle is in the cavity, detecting and analyzing signals transmitted by the cavity and assigning a classification to the particle in accordance with changes in the dielectric characteristics of the cavity caused by the presence of the particle.

2. A method according to claim 1 wherein the step of locating the particle includes locating the particle at least temporarily at the center of a cube shaped cavity.

3. A method according to claim 2, further including passing a stream of particles one by one through the center of the cavity in a direction extending from one corner of the cube-shaped cavity to a diagonally opposite corner thereof.

4. A method according to claim 1 wherein the step of locating the particle includes locating the particle on a support at the center of the cavity.

5. A method according to claim 1, further including passing a stream of particles one by one through the center of the cavity in a direction extending from a center of one face of the cube-shaped cavity to a center of an opposite face thereof.

6. A method according to claim 1 wherein the step of applying a swept frequency range of plane polarized electromagnetic radiation includes applying a swept frequency range of plane polarized electromagnetic radiation in the microwave part of the electromagnetic spectrum.

7. A method according to claim 1 wherein the particle is classified in accordance with a detected change in resonant frequency of the cavity, in amplitude of the transmitted signal at resonance, or in Q-factor.

8. Apparatus for classifying particles comprising a resonant cavity having a center, means for locating each particle at least temporarily at the center of the resonant cavity, means for applying a swept range of plane polarized electromagnetic radiation to the cavity in three mutually orthogonal directions while each particle is in the cavity, means for detecting and analyzing signals transmitted by the cavity, and means for assigning a classification to the particle in accordance with changes in dielectric characteristics of the cavity caused by the presence of the particle.

9. Apparatus according to claim 8 wherein the cavity is a cube-shaped cavity.

10. Apparatus according to claim 9 wherein the cube-shaped cavity has an entry opening at one corner of the cube-shaped cavity and an exit opening at a diagonally opposite corner of the cube-shaped cavity, and further including means for passing a stream of particles one by one through the center of the cavity in a direction from the entry opening to the exit opening.

11. Apparatus according to claim 9 wherein the cube-shaped cavity has entry and exit openings located centrally in opposite faces of the cube-shaped cavity, and further including means for passing a stream of particles one by one through the center of the cavity in a direction from the entry opening to the exit opening.

12. Apparatus according to claim 9, further including an access opening in one face of the cube-shaped cavity through which the particle can be introduced into the cavity, and a support for supporting the particle at the center of the cavity.

* * * * *